US 9,304,329 B2

(12) United States Patent
Zhao

(10) Patent No.: US 9,304,329 B2
(45) Date of Patent: Apr. 5, 2016

(54) PUPIL DEPENDENT DIFFRACTIVE LENS FOR NEAR, INTERMEDIATE, AND FAR VISION

(71) Applicant: Abbott Medical Optics Inc., Santa Ana, CA (US)

(72) Inventor: Huawei Zhao, Irvine, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 169 days.

(21) Appl. No.: 13/919,798

(22) Filed: Jun. 17, 2013

(65) Prior Publication Data

US 2013/0278891 A1  Oct. 24, 2013

Related U.S. Application Data

(62) Division of application No. 12/962,255, filed on Dec. 7, 2010, now abandoned.

(51) Int. Cl.
| | |
|---|---|
| *G02C 7/06* | (2006.01) |
| *G02C 7/04* | (2006.01) |
| *A61F 2/16* | (2006.01) |
| *G02B 5/18* | (2006.01) |

(52) U.S. Cl.
CPC .............. *G02C 7/041* (2013.01); *A61F 2/1618* (2013.01); *A61F 2/1654* (2013.01); *G02B 5/1895* (2013.01); *G02C 7/044* (2013.01); *G02C 7/06* (2013.01); *G02C 2202/20* (2013.01)

(58) Field of Classification Search
CPC ...... G02C 7/06; G02C 7/041; G02C 2202/20; A61F 2/1618; A61F 2/1654
USPC .............. 351/159.15, 159.44, 159.11, 159.35
See application file for complete search history.

(56) References Cited

U.S. PATENT DOCUMENTS

| | | | |
|---|---|---|---|
| 4,340,283 | A | 7/1982 | Cohen |
| 4,936,666 | A | 6/1990 | Futhey |

(Continued)

FOREIGN PATENT DOCUMENTS

EP         0393639  A2     10/1990

OTHER PUBLICATIONS

International Search Report and Written Opinion for Application No. PCT/US2011/063752, mailed on May 24, 2012, 23 pages.

(Continued)

*Primary Examiner* — Zachary Wilkes
(74) *Attorney, Agent, or Firm* — Abbott Medical Optics Inc.

(57) ABSTRACT

A multifocal diffractive lens comprises a multifocal diffractive structure coupled to a refractive component. The refractive component comprises at least one curved surface. The multifocal diffractive structure comprises a first plurality of substantially monofocal echellettes having a first optical power for near vision correction and a second plurality of substantially monofocal echellettes for far vision correction. The first plurality of substantially monofocal echellettes combined with the second plurality of substantially monofocal echellettes can provide a multifocal diffractive profile having decreased light scatter, chromatic aberration, and diffraction to non-viewing orders such that dysphotopsia is substantially inhibited. A third plurality of substantially monofocal echellettes having an intermediate optical power can be combined with the first plurality of substantially monofocal echellettes and the second plurality of substantially monofocal echellettes.

9 Claims, 8 Drawing Sheets

(56) References Cited

U.S. PATENT DOCUMENTS

| | | |
|---|---|---|
| 4,995,794 A | 2/1991 | Wycliffe |
| 5,017,000 A | 5/1991 | Cohen |
| 5,096,285 A | 3/1992 | Silberman |
| 7,188,949 B2 | 3/2007 | Bandhauer et al. |
| 7,455,404 B2 | 11/2008 | Bandhauer et al. |
| 2009/0195748 A1 | 8/2009 | Bandhauer et al. |
| 2009/0268155 A1 | 10/2009 | Weeber |
| 2009/0268158 A1 | 10/2009 | Weeber |
| 2010/0100178 A1 | 4/2010 | Weeber et al. |

OTHER PUBLICATIONS

Invitation to Pay Additional Fees and Where Applicable Protest Fee for Application No. PCT/US2011/063752, mailed Mar. 9, 2012, 5 pages.

PUPIL DEPENDENT DIFFRACTIVE LENS FOR NEAR, INTERMEDIATE, AND FAR VISION

RELATED APPLICATIONS

This application is a divisional of U.S. application Ser. No. 12/962,255 filed Dec. 7, 2010, which is incorporated herein by reference.

BACKGROUND OF THE INVENTION

1. Field of the Invention

The present invention relates to multifocal ophthalmic lenses to correct vision of an eye, such as multifocal intraocular lenses, multifocal contact lenses, and multifocal spectacles.

2. Description of Background Art

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only limited ability to change shape.

Along with reductions in accommodation of the eye, age may also induce clouding of the lens due to the formation of cataracts. Cataracts may form in the central nucleus of the lens, in the peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens (hereinafter "IOL").

A variety of prior technologies have been developed to enhance the ability of IOLs to facilitate viewing in presbyopic patients. For example, multifocal IOLs may rely on a diffractive optical surface to direct portions of the light energy toward differing focal distances, thereby allowing the presbyopic patient to see both near and far objects. Diffractive multifocal ophthalmic lenses have been proposed for treatments of presbyopia without removal of the natural crystalline lens, for example diffractive contact lenses.

A multifocal diffractive profile of the lens can be used to mitigate presbyopia by providing two or more optical powers, for example, one optical power for near vision and one optical power for far vision. These lenses may be in the form of a multifocal contact lens, for example a bifocal contact lens. The lenses may also take the form of an intraocular lens placed within the capsular bag of the eye, replacing the original lens.

Although multifocal diffractive ophthalmic lenses have improved the quality of vision for many presbyopic patients, additional improvements would still be beneficial. For example, at least some patients may experience unwanted light-related visual phenomenon (hereinafter "dysphotopsia") in at least some instances, such as halos from out of focus objects or optical effects that may be related to light scatter, for example, which can contribute to dysphotopsia. Diffractive multifocal lenses may direct visually significant amounts of light energy at other non-viewing foci, which can contribute to the unwanted light-related visual phenomenon experienced by the patient. Although multifocal diffractive lenses can be designed and optimized for a particular wavelength, people see in color and vision quality and light scatter can change at visible wavelengths away from the design wavelength such that vision quality may be less than ideal in at least some instances. The human eye responds to wavelengths of light within the visible spectrum having a range from about from about 400 nm to about 800 nm, and polychromatic light, for example white light, encompasses several wavelengths of visible light energy having wavelengths within this range. Although diffractive optics may work quite well at a design wavelength, for example at about 550 nm, the eye remains sensitive to light a wavelengths away from the design wavelength such as at about 500 nm and 600 nm, such that visual phenomenon may be observed with light away from the design wavelength in at least some instances.

A diffractive multifocal lens may have a diffractive profile that corresponds to a fraction of the design wavelength in at least some instances, such that light diffracts to multiple orders to provide the multifocal effect and mitigate presbyopia substantially. However, the diffraction of light to two or more orders with a diffractive profile that is a fraction of the design wavelength can be somewhat indirect and can diffract light to other adjacent orders such that patient vision can be less than ideal in at least some instances. Also, the diffraction of light to two or more orders from the profile can be at least somewhat sensitive to wavelength such that the amount of light diffracted to near and far focus can vary with wavelength in at least some instances. The optical properties of diffractive lenses can change with wavelength and viewing angle such that in at least some instances objects away from the optical axis of the eye can increase light scatter that can vary with wavelength and contribute to dysphotopsia in at least some instances.

Depth perception can be an important aspect of vision, and at least some of the prior multifocal lens may provide less depth perception than would be ideal in at least some instances. Intermediate vision correction can be helpful for depth perception and at least some of the prior diffractive optical lenses can provide less than ideal intermediate vision correction in at least some instances. For example, although apodization of a diffractive profile providing near and far vision correction has been proposed to provide increased relative amounts of light for far vision correction at larger pupil sizes, this approach can leave intermediate vision substantially uncorrected and result in wavelength dependent light scatter such that depth perception can be less than ideal in at least some instances.

In light of the above, it would be beneficial to provide improved multifocal lenses that overcome at least some of the limitations of the prior lenses. Ideally such improved lenses would provide diffractive multifocal lenses having diffractive profiles that improve the distribution of light energy distribution between viewing and non-viewing foci, vary the amount of light energy for near and far vision correction in a controlled manner in response to variation in pupil size, provide intermediate vision correction, decrease chromatic aberration, and decrease light scatter with off axis viewing so as to improve the quality of vision.

SUMMARY OF THE INVENTION

Embodiments of the present invention provide decreased light scattering and decreased chromatic aberration with a lens comprising a multifocal diffractive structure coupled to a surface of a refractive component, for example imposed on the surface, so as to provide improved patient vision at near and far viewing distances. The lens may comprise a foldable IOL having the diffractive structure imposed on the refractive component on a first side of the IOL. The multifocal diffractive structure may comprise a first plurality of substantially monofocal diffractive echellettes for near vision correction and a second plurality of substantially monofocal echellettes for far vision correction. The substantially monofocal echellettes can diffract transmitted light with an efficiency of at least about 90%. The first plurality of substantially monofocal echellettes for near vision correction can be combined with the second plurality of substantially monofocal echellettes for far vision correction so as to provide a distribution of near and far vision correction across the pupil having decreased light scatter, decreased chromatic aberration, and decreased diffraction to other orders such that dysphotopsia is substantially inhibited. The first plurality of substantially monofocal echellettes may comprise a first plurality of full period zones having radial sizes and locations based on the optical power of the near vision correction and design wavelength, and the second plurality of substantially monofocal echellettes may have second full period zones having radial sizes and locations corresponding to the first full period zones, and the second plurality of substantially monofocal echellettes can be placed on the second full period zones located between the first plurality of echellettes. The first plurality of substantially monofocal echellettes for near vision correction and the second plurality of substantially monofocal echellettes for far vision correction can be combined with a third plurality of substantially monofocal echellettes for intermediate vision correction such that near, far and intermediate vision correction can be provided with decreased light scatter, chromatic aberration and diffraction to other orders and dysphotopsia can be substantially inhibited. The first and third plurality of echellettes may comprise a first integer multiple of the design wavelength such as $1\lambda$, and the second plurality of echellettes may comprise a second integer multiple such as $0\lambda$. As the radial sizes and locations of the second zones of the second plurality of substantially monofocal echellettes and the third zones of the third plurality of substantially monofocal echellettes can correspond to the full period zones of the first plurality of substantially monofocal echellettes, the second plurality of substantially monofocal echellettes and third plurality of substantially monofocal echellettes can be arranged at locations corresponding to the first plurality of first full period zones so as to provide a multifocal diffractive lens component composed of substantially monofocal echellettes having a diffraction efficiency of at least about 90% of transmitted light to the near, intermediate and far optical corrections, such that dysphotopsia is inhibited substantially. Alternatively or in combination, the third plurality of echellettes may comprise multifocal echellettes, for example bifocal echellettes, combined with the first plurality of substantially monofocal echellettes and the second plurality of substantially monofocal echellettes.

The first plurality of substantially monofocal echellettes having the first substantially monofocal optical power can decrease light scatter, chromatic aberration and diffraction to other orders, so as to decrease substantially unwanted light-related visual phenomenon experienced by the patient. The first plurality of substantially monofocal echellettes may comprise a step height corresponding to an integer multiple of a design wavelength, for example within about +/−0.25λ of the integer multiple, such that at least about 90% of the transmitted light energy is diffracted with an optical power corresponding to the near vision correction. The integer multiple may comprise $1\lambda$, or $2\lambda$, or more. The first plurality of substantially monofocal echellettes can be combined with the second plurality of substantially monofocal echellettes in many ways so as to provide a multifocal lens with decreased light scattering and decreased chromatic aberration. For example, an inner portion of the lens may comprise an inner proportion of the first plurality of substantially monofocal echellettes to the second plurality of substantially monofocal echellettes, and an outer portion of the lens may comprise an outer proportion of the first plurality of substantially monofocal echellettes to the second plurality of substantially monofocal echellettes. The inner proportion can be greater than the outer proportion so as to provide relatively greater amounts of light for the near vision correction with the inner portion and relatively greater amounts of light for the far vision correction with the outer portion.

The first plurality of substantially monofocal echellettes may comprise substantially monofocal diffractive shape profiles located on the first portion of full period zones so as to diffract substantially at least about 90% of the light transmitted through the first plurality of echellettes to a diffractive order having an optical power corresponding to near vision correction, and so as to inhibit diffraction to other orders such that scattering and dysphotopsia are inhibited substantially. The substantially monofocal diffractive shape profiles may comprise a height corresponding substantially to an integer multiple of a design wavelength λ such that at least about 90%, for example 95% or more of the visible light transmitted through the first plurality of echellettes is diffracted to the order corresponding to the substantially monofocal near vision correction and so as to inhibit light scattering and diffraction to other adjacent orders. The integer may correspond to a positive diffractive order, for example +1, or +2, or more, such that chromatic aberration is corrected when light scattering from the diffractive structure is inhibited. The chromatic aberration corrected may comprise chromatic aberration from the at least one curved surface of the refractive component of the lens, or one or more components of the eye such as the cornea, the aqueous humor, or the crystalline lens, and combinations thereof.

The second plurality of substantially monofocal echellettes can provide the far vision correction. The second plurality of echellettes may comprise a step height that is an integer multiple of the design wavelength, for example to within about +/−0.25λ of the integer multiple, such that at least about 90% of the transmitted light energy is diffracted with an optical power corresponding to the far vision correction. The integer multiple may comprise $0\lambda$, or $1\lambda$, or more. The radial sizes and locations of the second plurality of echellettes may correspond to the full period zones, such that the second plurality of substantially monofocal echellettes can be located between the first plurality of substantially monofocal echellettes and diffract light for far vision correction.

The second plurality of substantially monofocal echellettes may comprise second diffractive shape profiles located on the second portion of the full period zones so as to provide a second optical power corresponding to far vision. The second diffractive profiles may corresponding to an integer multiple of the design wavelength, so as to provide a substantially monofocal far vision correction, such that light scattering, chromatic aberration and dysphotopsia can be inhibited substantially. For example, the integer multiple of the second plurality of echellettes may comprise zero for substantially monofocal far vision correction, such that diffraction to other orders, light scattering, chromatic aberration and dysphotopsia can be inhibited substantially.

The diffractive optical component may comprise a plurality of full period zones, and the first plurality of echellettes and the second plurality of echellettes can be arranged in many ways on the plurality of full period zones. The first plurality of substantially monofocal echellettes can be located on a first portion of the plurality of full period zones, and the second plurality of echellettes can be located on a second portion of the plurality of full period zones. Each full period zone may comprises a first half wave zone and a second half wave zone, the second half wave zone having an optical phase substantially opposite the first half wave zone.

The third plurality of substantially monofocal echellettes may comprise third diffractive profiles having a substantially monofocal intermediate diffractive optical power for intermediate vision correction located on a third portion of the plurality of full period zones so as to provide increased depth perception at intermediate viewing distances, for example. The third plurality of substantially monofocal echellettes comprising the third diffractive profiles can be configured so as to diffract at least about 90% of the transmitted light to the diffractive order corresponding to the substantially monofocal intermediate vision correction, such that light scatter, chromatic aberration and dysphotopsia from other orders are substantially inhibited and vision improved. The substantially monofocal diffractive shape profile may comprise a height corresponding substantially to an integer multiple of a design wavelength $\lambda$ such that at least about 90%, for example 95% or more of the visible light transmitted through the third plurality of substantially monofocal echellettes is diffracted to the order corresponding to a substantially monofocal near vision correction and so as to inhibit light scattering and diffraction to other orders. Each of the third plurality of substantially monofocal echellettes may have a width corresponding to a integer multiple of the widths of the first plurality of substantially monofocal echellettes, such as a multiple of two, three, or four, so that that the third plurality of substantially monofocal echellettes can be combined with the first and second plurality of substantially monofocal echellettes at locations across the pupil.

The intermediate vision correction may correspond to an amount of optical power within a range from about 0.25 to about 1.5 D of optical power added to the far vision correction, such that visual artifacts such as halos from objects at intermediate distances are decreased when the intermediate vision is provided with the enlarged pupil. The outer portion of the lens may comprise the third plurality of substantially monofocal echellettes having the substantially monofocal intermediate diffractive optical power and the second plurality of substantially monofocal echellettes having the substantially monofocal second diffractive optical power for far vision correction, so as to decrease light scatter, chromatic aberration and diffraction to other orders with the outer portion of the lens.

In a first aspect, embodiments of the present invention a lens to correct vision of an eye, the lens comprises a refractive component comprising at least one curved surface and a multifocal diffractive structure. The multifocal diffractive structure is optically coupled to the at least one curved surface. The multifocal diffractive structure comprises a first plurality of substantially monofocal echellettes having a first optical power corresponding to a near vision correction of the eye and a second plurality of substantially monofocal echellettes having a second optical power corresponding to a far vision correction of the eye.

In many embodiments, the diffractive structure is imposed on the at least one curved surface. Alternatively, the diffractive structure is imposed on a second component optically coupled to the refractive component.

In many embodiments, the first plurality of substantially monofocal of echellettes extends substantially around an inner boundary and an outer boundary of each of the substantially monofocal echellettes of the second plurality. The first plurality of substantially monofocal echellettes may comprise a first height corresponding to a non-zero integer multiple of a design wavelength and the second plurality of echellettes may comprise a second step height of about zero. The first plurality of substantially monofocal echellettes may extend substantially along the inner boundary and the outer boundary so as to define each of the second plurality of substantially monofocal echellettes.

In many embodiments, the first plurality of substantially monofocal echellettes comprises a first plurality of full period zones and the second plurality of substantially monofocal echellettes comprises a second plurality of full period zones corresponding to the first plurality of full period zones. The first plurality of substantially monofocal echellettes and an optical zone size of the diffractive structure may determine an integer number of full period zones, in which the integer number of full period zones comprises the first plurality of full period zones and the second plurality of full period zones. The first plurality of substantially monofocal echellettes can be determined based on the first diffractive optical power, the optical zone size, the design wavelength and a difference of an index of refraction of the eye and an index of refraction of the diffractive structure. The first plurality of substantially monofocal echellettes may comprise first substantially monofocal diffractive profiles extending substantially across the first plurality of full wave zones and the second plurality of substantially monofocal echellettes may comprise second substantially monofocal diffractive profiles extending substantially across the second plurality of full wave zones. The second plurality of full wave zones may have sizes and locations based on the first plurality of full wave zones.

In many embodiments, the first plurality of substantially monofocal echellettes has height profiles so as to diffract at least about 90% light transmitted energy to a first focus corresponding to the first optical power for near vision correction, and the second plurality of substantially monofocal echellettes may have height profiles so as to diffract at least about 90% light transmitted energy to a second focus corresponding to the second optical power for near vision correction.

In many embodiments, the lens further comprises a third plurality of substantially monofocal echellettes. The third plurality of substantially monofocal echellettes has third heights and third full period zones at third locations corresponding to the first plurality of substantially monofocal echellettes, and the third plurality of substantially monofocal echellettes has a third optical power corresponding to an intermediate vision of the patient. The third plurality of substantially monofocal echellettes may have heights approximating heights of the first plurality of substantially monofocal echellettes, and the third plurality of substantially monofocal echellettes may have widths corresponding to an integer multiple of two or more widths of the full period zones of the first plurality of substantially monofocal echellettes.

In many embodiments, the diffractive structure comprises an inner portion and an outer portion. The inner portion comprises an inner proportion of the first plurality of substantially monofocal echellettes to the second plurality of substantially monofocal echellettes, and the outer portion comprises an outer proportion of the first plurality of substantially monofocal echellettes to the second plurality of substantially monofocal echellettes. The outer proportion may be less than the inner proportion so as to provide near vision correction with the inner portion and far vision correction with outer portion when the pupil responds to light.

In many embodiments, the diffractive structure has full wave zones comprising pairs of half period zones. Each of the pairs comprises an inner half period zone having an inner phase and an outer half period zone having an outer phase opposite the inner phase. A third plurality of echellettes may comprise pairs of echellettes, in which each pair has an inner echellette extending substantially across the inner half period zone and an outer echellette extending substantially across the outer half period zone. The pairs of echellettes of the third plurality may correspond to the intermediate vision correction and the far vision correction. The inner echellette of said each pair of the third plurality of echellettes may correspond to the far vision correction and said outer echellette of said each pair of the third plurality of echellettes may correspond to the intermediate vision correction. The inner echellette of said each pair of the third plurality of echellettes may correspond to the intermediate vision correction and said outer echellette of said each pair of the third plurality of echellettes may corresponds to the far vision correction.

In another aspect embodiments provide a method of correcting vision of an eye. A lens is placed along an optical path of the eye. The lens comprises at least one curved surface coupled to a diffractive structure. The diffractive structure comprises a first plurality of substantially monofocal echellettes having a first optical power for a near vision correction and a second plurality of substantially monofocal echellettes having a second optical power for a far vision correction. The first plurality of substantially monofocal echellettes diffracts transmitted light with a first efficiency of at least about 90% for the near vision correction and the second plurality of substantially monofocal echellettes diffracts transmitted light with an efficiency of at least about 90% for the far vision correction.

In many embodiments, the first plurality of substantially monofocal echellettes has a corresponding first plurality of full period zones and second plurality of substantially monofocal echellettes has a second plurality of full period zones corresponding to the first plurality of full period zones.

In many embodiments, the diffractive structure comprises a third plurality of substantially monofocal echellettes having an intermediate optical power for an intermediate vision correction. The third plurality of substantially monofocal echellettes has third heights approximating first heights of the first plurality of substantially monofocal echellettes. The third plurality of substantially monofocal echellettes has a third plurality of full period zones corresponding to the first plurality of full period zones. The first plurality of full period zones has first widths and the third plurality of full period zones has third widths. The third widths corresponding to an integer multiple of two or more of the first widths, such that first optical power corresponds to the width integer multiple multiplied with the third optical power.

DETAILED DESCRIPTION OF THE INVENTION

Figure 1A:
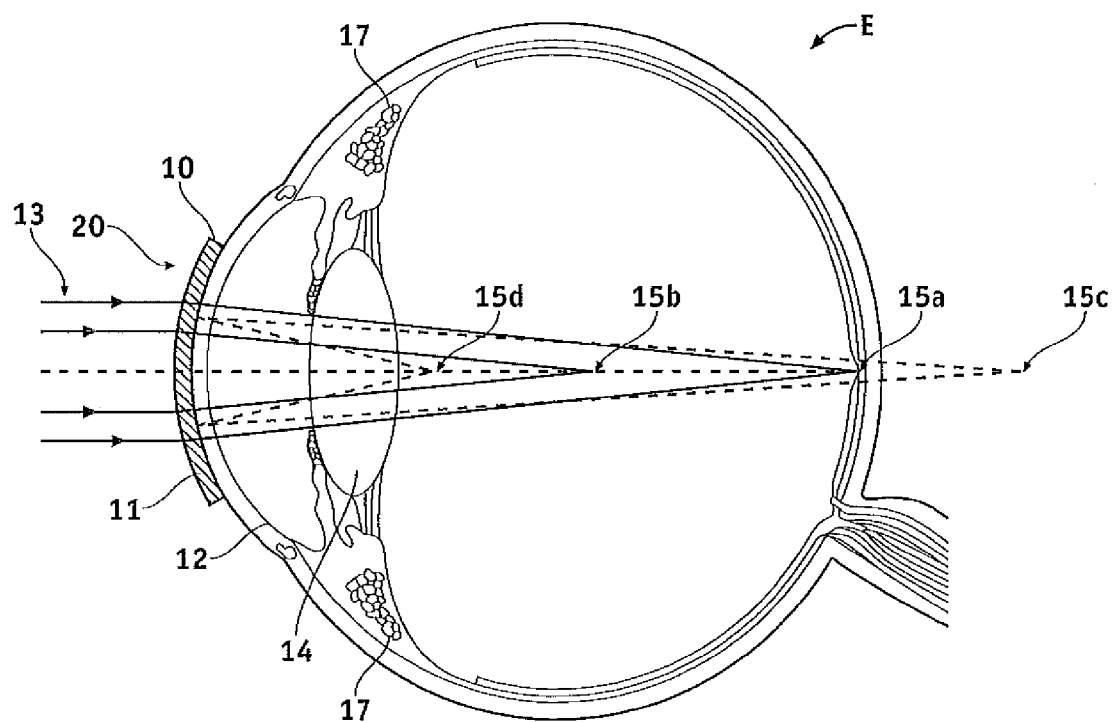
FIG. 1A is a cross-sectional view of an eye with an ophthalmic lens comprising multifocal contact lens having a diffractive structure, in accordance with the embodiments of the present invention.

Embodiments of the present invention as described herein generally provide improved lenses and imaging systems. Although embodiments of the present invention may find their most immediate use may be in the form of improved ophthalmic devices, systems, and methods, the diffractive structures as described herein can be used with many optical systems such as imaging systems and viewing systems. Exemplary embodiments of the present invention provide improved ophthalmic lenses (including, for example contact lenses, intraocular lenses, corneal lenses, spectacle lenses, and combinations thereof and the like) and associated methods for their design and use. Embodiments of the present invention include multifocal diffractive lenses, such bifocal diffractive lenses with near vision correction and far vision correction, and trifocal diffractive lenses comprises near, intermediate and far vision correction, for example. Exemplary embodiments provide multifocal diffractive ophthalmic lenses having a first plurality of substantially monofocal echellettes having a first optical power for near vision correction and a second plurality of substantially monofocal echellettes having a second optical power for far vision correction, so as to reduced light scatter and improve the light energy distribution such that viewing performance is enhanced. The diffractive surface can be optically smooth to reduce scatter and may comprise echellettes having rounded profiles, for example with transition zones to smooth the surface profile transition between echellettes.

Diffractive structures on ophthalmic lenses as described herein may use a first plurality of substantially monofocal echellettes having first order diffraction with a first optical power for near vision order and a second plurality of substantially monofocal echellettes having zero order diffraction with a second optical power for far vision, such that light scatter can be reduced, for example with a bifocal correction. Alternatively or in combination, the first plurality of substantially monofocal echellettes having second order diffraction for near vision correction, the second plurality of substantially monofocal echellettes for zero order diffraction, and a third plurality of substantially monofocal echellettes for intermediate vision correction can be combined so as to provide a multifocal diffractive structure for far vision correction, intermediate vision correction and near vision correction having reduced light scatter. In many embodiments, the amount of light energy diffractive to the viewing orders comprises at least about 90% of the transmitted light energy, for example at least about 90% of the visible polychromatic light energy transmitted through the diffractive structure under many viewing conditions such as with natural or artificial light and combinations thereof.

Although some small portion of the light energy may also be diffracted to other, non-viewing orders, the amount of light energy diffracted to such orders can be inhibited substantially in accordance with embodiments as described herein, such as embodiments having substantially monofocal echellettes for near vision correction combined with substantially monofocal echellettes for far vision correction.

As used herein, the term "non-viewing order" encompasses a diffractive order containing energy that is not useful in forming an image on the retina of an eye such as at near, intermediate or far viewing distances, for example.

As used herein, the term "multifocal" encompasses two or more optical powers to focus light on the retina.

As used herein, the term "bifocal" encompasses two optical powers to focus light on the retina.

By recognizing that a first plurality of substantially monofocal echellettes having an optical power for near vision correction can be combined with a second plurality of substantially monofocal echellettes to provide a multifocal diffractive structure such as a lens, light energy transmitted to non-viewing orders can be decreased substantially. For example, the first plurality of substantially monofocal echellettes having the optical power and diffractive order for near vision correction at the design wavelength can be used to determine a plurality of full period zones. A first portion of the plurality of full period zones may comprise the first plurality of the substantially monofocal echellettes for near vision correction, and a second portion of the plurality of full period zones may comprise the second plurality of substantially monofocal for far vision correction, such that the substantially monofocal echellettes can be positioned on the full wave zones to provide pupil dependent diffractive optical power with decreased light scatter.

The diffractive structures of the embodiments of the present invention as described herein may also provide additional advantages by enhancing the design flexibility through selectively locating the first echellettes of the first plurality substantially monofocal echellettes and the second echellettes of the second plurality of substantially monofocal echellettes so as to benefit overall viewing performance. For example, arranging the locations of the substantially monofocal near vision echellettes and the substantially monofocal far vision echellettes on the plurality of full period zones can provide a multifocal diffractive structure with at least 90% of light energy transmitted to viewing orders and vary the amount of light energy to near and far vision correction as the pupil size changes. Reading is often done in bright light conditions in which the pupil is small, and in at least some instances the pupil size may decrease when the eye accommodates so as to decrease a size of the pupil. In contrast, nighttime driving is done in low light conditions in which the pupil is large. It may be advantageous to vary the proportion of the near vision echellettes to far vision echellettes radially across the pupil so that different light amounts of light energy are provided for each vision correction based on the viewing situation and resulting pupil size. In some such ophthalmic lenses, an outer portion of the diffractive structure may comprise a greater proportion of substantially monofocal far vision echellettes to substantially monofocal near vision echellettes, such that a majority of the light energy transmitted through the outer portion may be diffracted to the far focus so as to accommodate for low light, far viewing conditions such as night time driving. An inner portion of the diffractive structure may comprise a greater proportion of substantially monofocal near vision echellettes to substantially monofocal far vision echellettes, such that a majority of the light energy transmitted through the inner portion may be diffracted to the near focus so as to accommodate for near viewing with increased illumination. Intermediate vision correction may be provided with a third plurality of substantially monofocal intermediate vision echellettes having an intermediate optical power located in the outer portion of the lens, for example. Varying radially the proportion of the substantially monofocal echellettes corresponding to each of near, far and intermediate vision may thus provide diffractive multifocal structure having separate diffractive full period zones that separately correct each of near, far and intermediate vision, respectively, and which vary the corresponding amount of light energy distributed to each of near, far, and intermediate vision correction over the diffractive structure as the pupil changes in size. As the diffractive structure comprises substantially monofocal echellettes, the amount of light energy diffracted to the near, far, and intermediate optical powers and corresponding orders may comprise at least 90% of transmitted light energy.

FIG. 1A is a cross-sectional view of an eye E fit with an ophthalmic lens 20 comprising a multifocal diffractive contact lens 11 having a multifocal diffractive structure 10 comprising a first plurality of substantially monofocal echellettes for near vision correction and a second plurality of substantially monofocal echellettes for far vision correction. Multifocal diffractive contact lens 11 may, for example, comprise a bifocal contact lens. Multifocal diffractive contact lens 11 covers at least a portion of cornea 12 at the front of eye E and can be centered about the optical axis of eye E.

Each major surface of ophthalmic lens 20 such as contact lens 11, including the anterior (front) surface and posterior (back) surface, generally has a refractive profile. The two surfaces together, in relation to the properties of the air, tear film, cornea, and other optical components of the overall optical system, define the optical effects of the lens 11 on the imaging performance by eye E. Conventional, monofocal contact lenses have a refractive power based on the refractive index of the material from which the lens is made, and also on the curvature or shape of the front and rear surfaces or faces of the lens, and can be combined with the multifocal diffractive structure 10 having the substantially monofocal echellettes in accordance with embodiments as described herein. The diffractive structure 10 can be optically coupled to at least one curved surface of lens 11 having the refractive optical power, and the diffractive structure 10 may be imposed on the surface having the refractive power so as to couple the diffractive structure to the at least one curved surface of lens.

In a young, healthy eye contraction and relaxation of ciliary muscles 17 surrounding the natural lens 14 contribute to accommodation of the eye, the process by which the eye increases optical power to maintain focus on objects as they move closer. As a person ages, the degree of accommodation decreases and presbyopia, the diminished ability to focus on near objects, often results. A patient may therefore benefit corrective optics having at least two optical powers, one for near vision and one for far vision, as provided by multifocal contact lens 11, for example.

The ophthalmic lens 20 may combine the multifocal diffractive structure 10 with the refractive properties of the lens 20. Such lenses may include different diffractive optical powers in different regions of the lens 20 so as to mitigate the effects of presbyopia. For example, as shown in FIG. 1A, an outer portion of refractive multifocal diffractive contact lens 11 may have an optical power which is suitable for viewing at far viewing distances. The multifocal diffractive contact lens 11 may also include an inner portion having a higher optical power (sometimes referred to as a positive add power) suitable for viewing at near distances.

The multifocal diffractive ophthalmic lens 20, such as contact lenses or IOLs, can have a refractive optical power combined with a diffractive optical power. The diffractive optical power can, for example, comprise positive add power, and the add power may be a significant (or even the primary) contributor to the overall optical power of the lens. The diffractive optical power may be provided by a plurality of substantially concentric diffractive echellettes located at zones, in which each echellette may comprise a diffractive profile located at the corresponding zone. The diffractive structure may either be imposed on the anterior surface, or posterior surface, or both.

The diffractive structure 10 of the diffractive ophthalmic multifocal lens 20 comprises a first plurality of substantially monofocal echellettes for near vision correction and a second plurality of substantially monofocal echellettes for far vision correction, and can diffract incoming light to two or more diffraction orders. As light 13 enters from the front of the eye, multifocal contact lens 11 and the natural lens 14 bend light 13 to form a far field focus 15$a$ on retina 16 for viewing for distant objects and a near field focus 15$b$ for objects close to the eye. Depending on the distance form the source of light 13, the focus on retina 16, the viewing focus, may be near field focus 15$b$ instead. Far field focus 15$a$ can correspond with $0^{th}$ diffractive order from the second plurality of substantially monofocal echellettes having the second optical power for far vision correction, and near field focus 15$b$ can correspond to the $1^{st}$ diffractive order from the first plurality of substantially monofocal echellettes having the first optical power for near vision correction.

Multifocal ophthalmic lens 20 of contact lens 11 may comprise the bifocal lens and distribute a majority of light energy into the two viewing orders with the first plurality of substantially monofocal echellettes and the second plurality of substantially monofocal echellettes. The amount of near viewing light energy and far vision light energy can be proportioned based on the proportion of substantially monofocal near vision echellettes to far vision echellettes, for example proportioned evenly with a 1:1 near vision echellette to far vision echellette ratio corresponding to a 50%:50% near vision to far vision light energy ratio. The diffractive structure 10 comprising of the combination of substantially monofocal echellettes can direct a significant portion of the incident light energy to viewing orders such that diffraction to into other, non-viewing diffractive orders 15$c$ and 15$d$ is substantially inhibited. The non-viewing orders 15$c$ and 15$d$ may comprise $-1^{st}$ and $+2^{nd}$, respectively. In many bifocal embodiments, the first plurality of substantially monofocal echellettes having the $1^{st}$ order diffraction corresponding to the near vision correction and the second plurality of substantially monofocal echellettes having $0^{th}$ order diffraction corresponding to the far vision correction diffract at least about 90% of the transmitted light to the $0^{th}$ order and the $1^{st}$ order such that diffraction to non-viewing orders is inhibited substantially. In many embodiments having the exemplary diffractive bifocal correction, the non-viewing orders may comprise the $2^{nd}$, $3^{rd}$, $-1^{st}$, $-2^{nd}$, $-3^{rd}$ diffractive orders, for example. The remaining percentage of the transmitted light energy is received by the higher and lower orders, and the $-1^{st}$ and $2^{nd}$ order may each receive no more than about 2.5% of the light energy for such bifocal diffractive lenses.

Figure 1B:
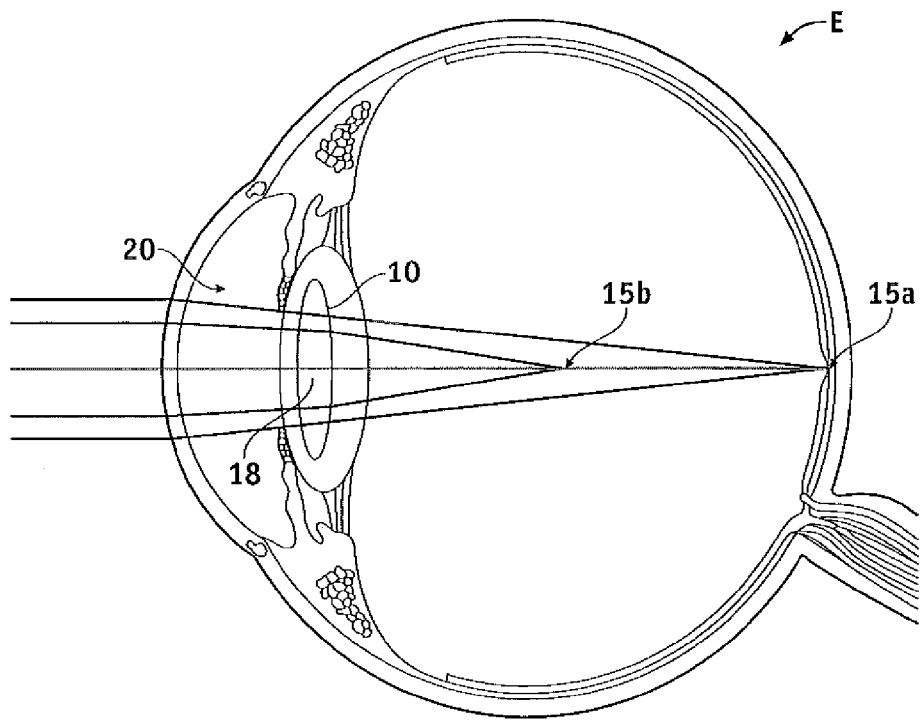
FIG. 1B is a cross-sectional view of an eye having an ophthalmic lens comprising an implanted multifocal intraocular lens having a bifocal diffractive structure, in accordance with embodiments of the present invention.

The ophthalmic lens 20 and diffractive structure 10 may comprise many additional types of multifocal ophthalmic lenses such as multifocal intraocular lens (IOL) 18 shown in FIG. 1B. For patients with IOLs, natural lens 14 is removed and IOL 18 is placed within capsular bag 19 in eye E. IOL 18 is centered about the optical axis of the eye E. Like multifocal contact lens 11, IOL 18 often has a refractive power and may comprise multifocal diffractive structure 10 having first plurality of substantially monofocal echellettes with a first optical power for near vision and a second plurality of substantially monofocal echellettes with a second optical power for far vision. Similar to contact lens 11, IOL 18 can focus incoming light 13 to far field focus 15$a$ with the second optical power and near field focus 15$b$ with the first optical power.

Figure 1C:
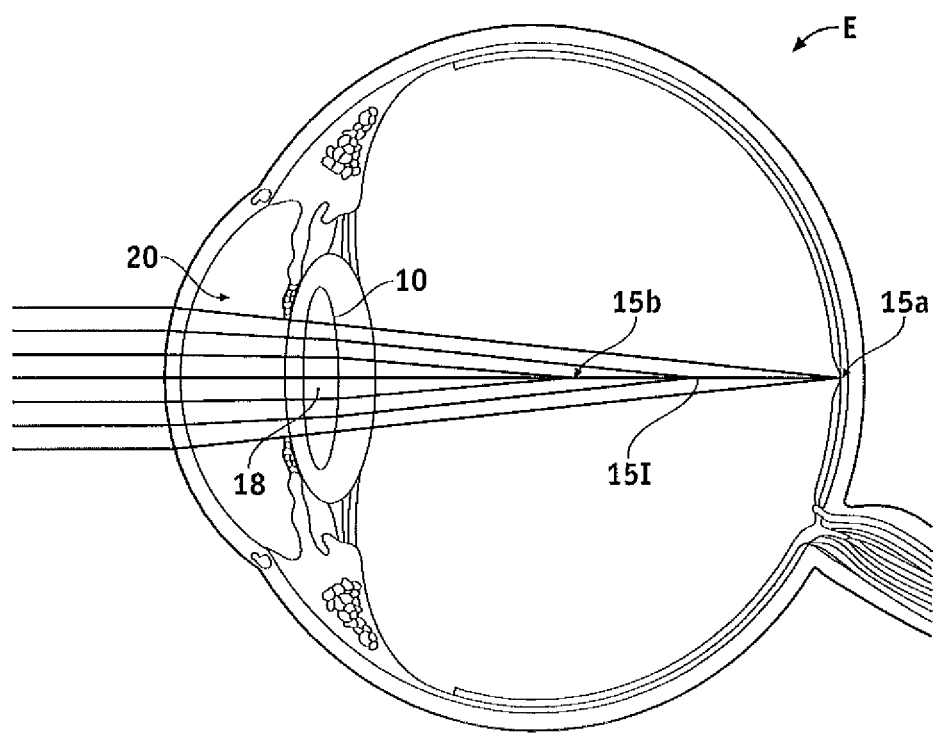
FIG. 1C is a cross-sectional view of an eye having ophthalmic lens comprising an implanted multifocal intraocular lens having a trifocal diffractive structure suitable for incorporation, in accordance with the embodiments of the present invention.

FIG. 1C is a cross-sectional view of an eye having an implanted multifocal intraocular lens in which diffractive structure 10 comprises a first plurality of substantially monofocal echellettes having a first optical power for near vision correction, a second plurality of substantially monofocal echellettes having a second optical power for far vision correction, and a third plurality of substantially monofocal echellettes having a third optical power for intermediate vision correction. The trifocal diffractive lens can comprise diffractive profiles such that the far focus comprises 15A, the intermediate focus comprises 15I and the near focus comprises 15B, for example. The far focus 15A, intermediate focus 15I and near focus 15B may correspond to zero order diffraction, first order diffraction and second order diffraction, respectively. The contact lens as described above may comprise the trifocal configuration, for example. The near focus may correspond to an add optical power vision correction of about +3D, for example. The intermediate focus may correspond to an add optical power vision correction of about 1.5 D, for example, and the far focus may correspond to an add optical power of about 0 D, for example.

Figure 2A:
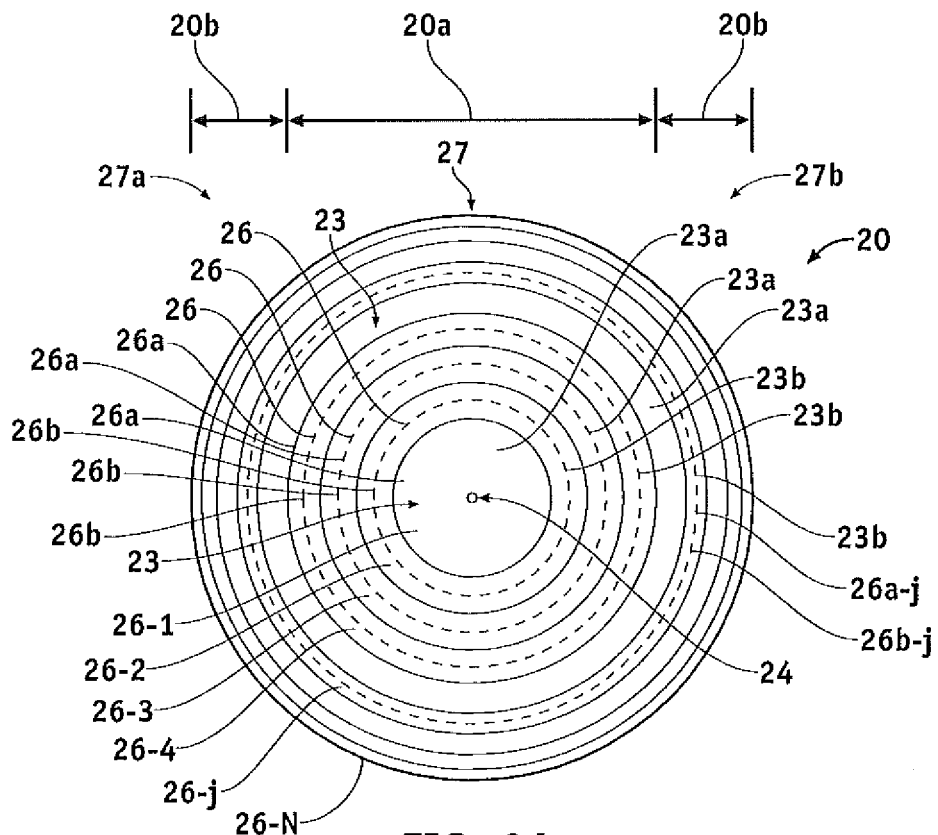
FIG. 2A is a front view of a multifocal ophthalmic lens in accordance with embodiments of the present invention.
Figure 2B:
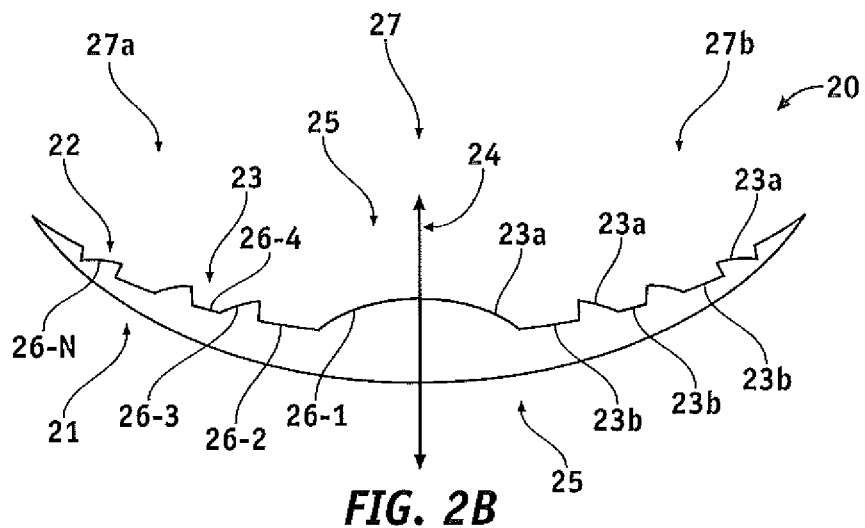
FIG. 2B is a cross-sectional view of the lens of FIG. 2A.

FIGS. 2A and 2B show the diffractive structure 10 of the multifocal diffractive ophthalmic lens 20 that may comprise the multifocal contact lens 11 or IOL 18 described above. The multifocal ophthalmic lens 20 may comprise at least one refractive surface defined with one or more or a radius of curvature, an apical radius of curvature, a conic constant, a fourth order spherical aberration, a sixth order spherical aberration or an optical path distance elevation based on wavefront aberration measurement of the eye, so as to provide optical correction of the eye. Multifocal lens 20 has an anterior lens surface 21 and a posterior lens surface 22 disposed about optical axis 24. The surfaces 21, and surface 22 of lens 20 typically define a clear aperture 25 corresponding to the optically used portion of lens 20. The optically used portion of lens 20 having diffractive structure 10 comprises an inner portion having dimension 20A across and an outer portion having annular dimension 20B. The inner portion having dimension 20A may correspond to a bifocal correction, for example with a greater proportion of near vision substantially monofocal echellettes to far vision substantially monofocal echellettes. The outer portion having annular dimension 20B may correspond to trifocal correction, for example with near vision correction, intermediate vision correction and far vision correction. The outer portion having annular dimension 20B may have a greater proportion of far vision and intermediate vision substantially monofocal echellettes to near vision substantially monofocal echellettes.

The diffractive structure 10 of diffractive ophthalmic lens 20 comprises a plurality of full period zones 26 that correspond to the locations of the echellettes of lens 20. The plurality of full period zones may comprise N full period zones, for example up from the first full period zone, 26-1, the second full period zone 26-2, the third full period zone 26-3, the jth full period zone 26-j, up to the Nth full period zone 26-N zone. Each of the plurality of full period zones 26 may comprise a first half period zone 26A and a second half period zone 26B. The jth full period zone 26-j comprises a first have period zone 26A-jth and a second half period zone 26B-jth. The full period zones of the first diffractive profile may correspond to the full period zones of the second diffractive profile, such that the echellettes of the first profile can be located between echellettes of the second profile.

The radial locations of the plurality of full period zones 26 of diffractive structure 10 can be determined based on the first order distance corresponding to the add optical power for near vision correction Da and the design wavelength λ with the relationship $$r_n \approx \sqrt{(2jd\lambda)}$$

where $r_n$ is the outer boundary of the full period zone, j is the number of the zone, d is the first order diffraction distance corresponding to the add power for near vision correction and λ is the design wavelength. The exact radial locations of the boundaries can be determined based on the curvature of the cornea, the index of refraction of the aqueous humor of the eye and the axial length of the eye with equations known to those of ordinary skill in the art. The first order distance d can be determined with the equation $$d = 1/Da$$

and the first order distance d is inversely related to the add optical power for near vision correction. For example, when Da is +3D corresponding to +3D of optical add power, d equals 0.333.

The plurality of full period zones 26 can be determined based on the add optical power Da, such that the widths and locations of the second plurality of echellettes correspond to the first plurality of echellettes and such that the plurality of full period zones 26 comprises the first plurality of full period zones of the first plurality of substantially monofocal echellettes and the full period zones of the second plurality of substantially monofocal echellettes.

When fitted onto the eye of a subject or patient, the optical axis of lens 20 is generally aligned with the optical axis of eye E. The curvature of lens 20 gives lens 20 an anterior refractive profile and a posterior refractive profile. The diffractive structure 10 may be imposed on either anterior surface 21, or posterior surface 22 or both. FIG. 2B shows the diffractive structure 10 imposed on the posterior surface 22. The first plurality of substantially monofocal echellettes 23A have first substantially monofocal diffractive profiles corresponding to the first substantially monofocal diffractive profile 27A.

The first substantially monofocal diffractive profile 27A may comprise the first plurality of substantially monofocal echellettes 23A and a second diffractive profile 27B may comprise the second plurality of substantially monofocal echellettes 23B. The first plurality of substantially monofocal echellettes may be located at first full period zone 26-1, third full period zone 26-3, etc., so as to define the first substantially monofocal diffractive profile with the first plurality of substantially monofocal echellettes, and the second plurality of echellettes may be located at second full period zone 26-2, fourth full period zone 26-4, etc., so as to define the second diffractive profile with the second plurality of substantially monofocal echellettes. The first plurality of substantially monofocal echellettes may comprise a first step height, for example corresponding to an integer multiple K of the design wavelength (Kλ), and the second plurality of substantially monofocal echellettes may comprise a second step height. The first step height may comprise about 1λ and the second step height may comprise about 0λ, for example. The first plurality of substantially monofocal echellettes may extend substantially around each of the second plurality of substantially monofocal echellettes so as to define the second plurality of substantially monofocal echellettes, for example when the second plurality of substantially monofocal echellettes comprises a step height of about 0λ and the first plurality of substantially monofocal echellettes comprises the step height of about 1λ.

Figure 3A:
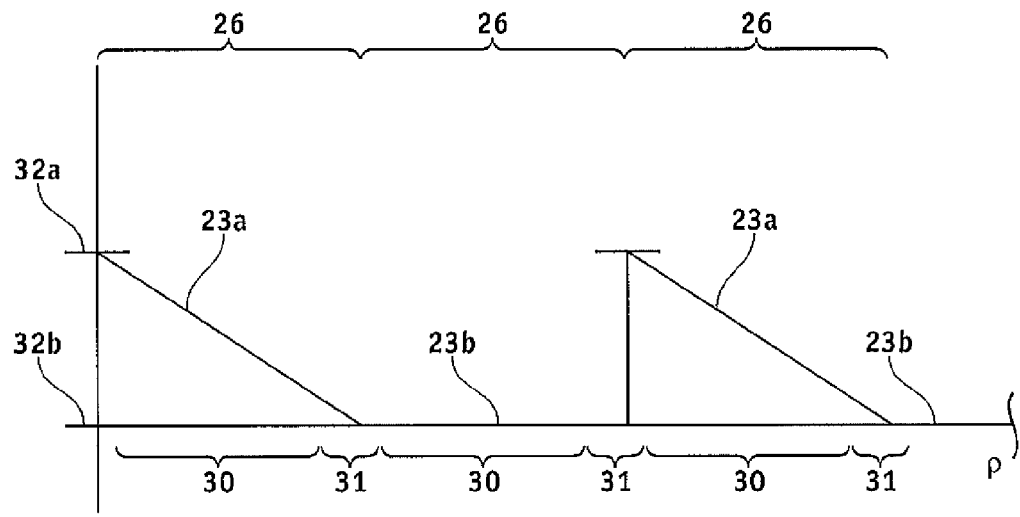
FIGS. 3A-3B are graphical representations of a portion of the diffractive profile of a multifocal lens suitable for incorporation in accordance with embodiments as described herein.
Figure 3B:
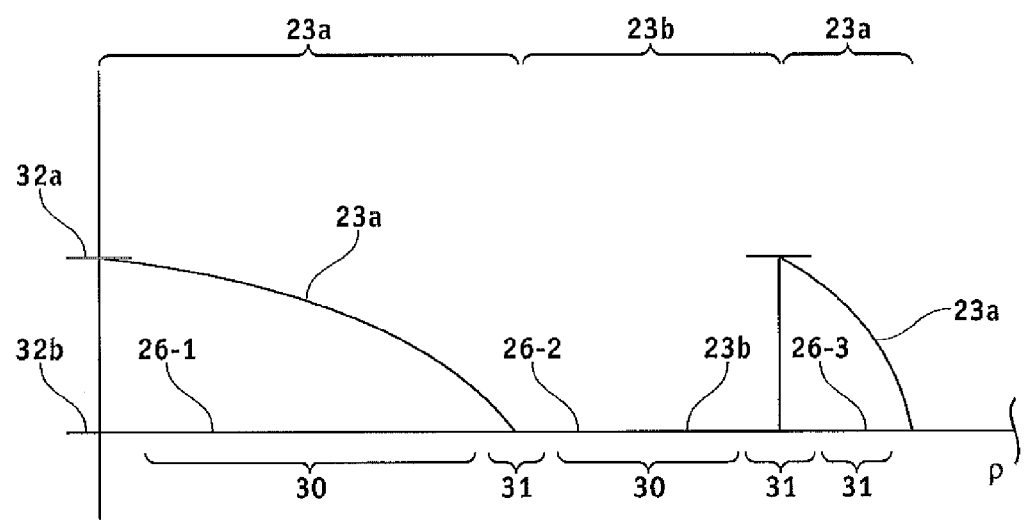

FIGS. 3A and 3B are graphical representation of a portion of the diffractive profile of diffractive structure 10 of multifocal lens 20. In FIG. 3A, the displacement (from the optical axis or another reference point on a plane perpendicular to the optical axis) of each point on the echellette surface is plotted against the square of the radial distance ($r^2$ or p) from the optical axis of the lens. In conventional multifocal lenses, each echellette 23 may have a diameter or distance from the optical axis which is often proportional to √j, j being the number of the echellette 23 as counted from optical axis 24. Each echellette may have a characteristic optical zone 30 and transition zone 31. Optical zone 30 may have a shape or downward slope that may be linear when plotted against p as shown in FIG. 3A. When plotted against radius r, optical zone 30 may have a shape or downward slope that is parabolic as shown in FIG. 3B. The diffractive shape profile comprising the height and slope of optical zone 30 can determine the optical add power of each of profile 27A and profile 27B of lens 20.

As shown in FIGS. 3A and 3B, the echellettes have a step height and transition zone 31 can extend between adjacent echellettes. The transition zone 31 may be sharp and discontinuous. Alternatively, the transition zone may provide a smooth transition between a first optical zone 30 and a second optical zone 31. The first plurality of echellettes or the second plurality of echellettes, or both, may be smoothed so as to improve efficiency of diffraction. The smoothing of echellettes is described in U.S. Pat. No. 4,995,794, and U.S. Pub. No. 2009/0268158, the disclosures of which may be suitable for combination in accordance with at least some embodiments as described herein.

The first plurality of echellettes 23A may have a characteristic first step height 32A defined by the distance between the lowest point and height point of the echellette. The slope (or first derivative) and/or the curvature (second derivative) of the diffractive surface may discontinuous adjacent the transitions. For the substantially monofocal first diffractive profile, the first plurality of echellettes may correspond to a first integer multiple (K1) of a design wavelength $\lambda$, for example $1\lambda$, so as to provide the near vision optical correction.

The second plurality of echellettes may have a second step height 32B that may be less than the first step height 32A. The far vision correction provided by the second plurality of echellettes may correspond to a second integer multiple (K2) of the design wavelength $\lambda$, for example $0\lambda$, or a portion of the first integer multiple (K1) such as a fraction of the first integer multiple, e.g. $\lambda/2$.

When the second step height 32B of the second plurality of echellettes corresponds to an integer multiple of the design wavelength, the second plurality of echellettes and the second diffractive profile may comprise a substantially monofocal profile. For example, the first plurality of echellettes may comprise a first step height 32A having K1=2 and corresponding to $2\lambda$, and the second plurality of echellettes may comprise a second step height 32B having K2=1 and corresponding to $1\lambda$, for example.

The light energy distribution between different diffractive orders is dependent on wavelength $\lambda$, the depth of step height, and the difference ($\Delta\eta$) between the refractive index of the lens (n1) and the refractive index of the surrounding medium (n2). For example, step height 32A corresponding to $\lambda$ with a physical step height of $(\lambda/\Delta\eta)$ will distribute the majority of light energy to the $1^{st}$ order, which corresponds to the near field, and will be substantially monofocal. At a step height of greater than $\lambda/(2\Delta\eta)$, there will be greater amounts of light energy distributed to the $1^{st}$ order than the $0^{th}$ order, which corresponds to the far field. At a depth of less than $\lambda/(2\Delta\eta)$, light energy is distributed more towards the $0^{th}$ order.

A step height 32B of $\lambda/(2\Delta\eta)$ can be used for the second plurality of echellettes so as to provide a second diffractive profile that is multifocal. At this depth, light energy at the wavelength $\lambda$ can be distributed evenly between the $1^{st}$ and $0^{th}$ orders, for example at least about 40% each. When the first substantially monofocal diffractive profile providing near vision correction corresponds to $1\lambda$ and comprises first step height 32A of $\lambda/(\Delta\eta)$, the proportion of the first plurality of monofocal echellettes to the second plurality of multifocal echellettes can be varied radially so as vary the amount of energy light energy having near vision correction and the amount of light energy having far vision correction.

Figure 4A:
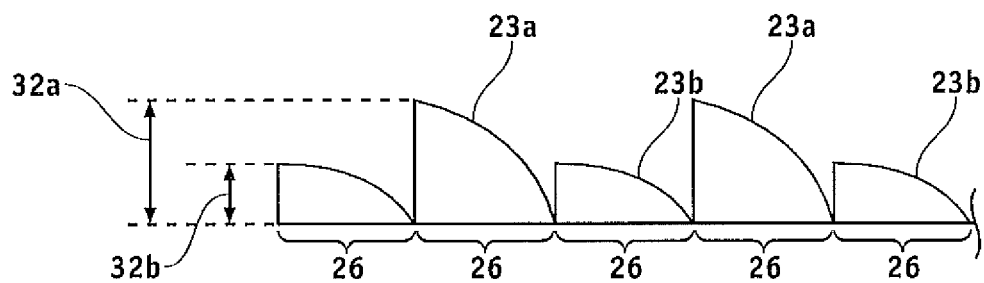
FIG. 4A shows a portion of diffractive profile comprising a first plurality of substantially monofocal diffractive echellettes for near vision correction and a second plurality of bifocal echellettes for far vision correction and near vision correction, in accordance with embodiments.

FIG. 4A shows a portion of a diffractive profile of diffractive structure 10 comprising the first plurality of echellettes 23A having substantially monofocal diffractive profiles for near vision correction and a second plurality of echellettes 23B having substantially bifocal diffractive profiles for far vision correction and near vision correction. The first step height 32A has K1=1 and corresponds to $1\lambda$ with a physical step height of about $\lambda(\Delta\eta)$. The first plurality of echellettes having the first substantially monofocal diffractive profile can diffract at least about 90% of the transmitted polychromatic visible light energy to the near focus, for example at least about 95%, for example at least about 97%, and in some embodiments may diffract 99% or more of the transmitted polychromatic visible light energy. The second step height 32B has K2=½ and corresponds to $\lambda/2$ and comprises a physical step height of about $\lambda/(2\Delta\eta)$. The second plurality of echellettes can diffract at least about 45% of the light energy to the near focus and at least about 45% of the light energy to the far focus. The height of the second plurality of echellettes can be varied so as to diffract more light energy to the far focus and less light energy to the near focus, or less light energy to far and more to near, based on the step height as described above.

The multifocal diffractive profile comprising the first plurality of substantially monofocal echellettes and the second plurality of echellettes as shown in FIG. 4A can be well suited for use in the inner portion of the lens corresponding to dimension 20A as shown above so as to provide the inner portion with a majority amount of light near vision correction and a minority amount of light for far vision correction.

Figure 4B:
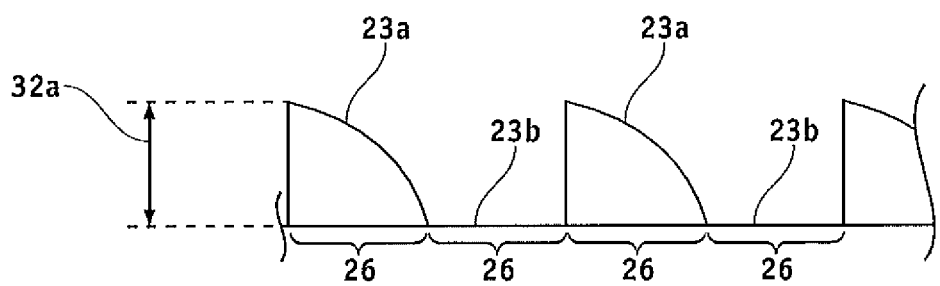
FIG. 4B shows a portion of a diffractive profile comprising a first plurality of substantially monofocal diffractive echellettes for near vision correction and a second plurality of substantially monofocal diffractive echellettes for far vision correction, in accordance with embodiments.

FIG. 4B shows a portion of a diffractive profile of diffractive structure 10 comprising the first plurality of substantially monofocal echellettes 23A having substantially monofocal diffractive profiles for near vision correction and the second plurality of substantially monofocal echellettes 23B having substantially monofocal diffractive profiles for far vision correction. The first step height 32A has K1=1 and corresponds to $1\lambda$ with a physical step height of about $\lambda/(\Delta\eta)$, as described above. The second step height 32B has K1=0 and corresponds to $0\lambda$, with a physical step height of about 0 and can diffract light to the $0^{th}$ order corresponding to the far vision correction. The second plurality of echellettes can be located at a second portion of full wave zones defined with the first plurality of echellettes so as to diffract light to the $0^{th}$ order corresponding to the far vision correction. The second plurality of substantially monofocal echellettes having the second substantially monofocal diffractive profile can diffract at least about 90% of the polychromatic visible light energy to the far focus, for example at least about 95%, for example at least about 97%, and in some embodiments may diffract 99% or more of the polychromatic visible light energy.

The multifocal diffractive profile comprising the first plurality of substantially monofocal echellettes for near vision correction and the second plurality of substantially monofocal echellettes far vision correction, for example as shown in FIG. 4B, can be used to provide near and far vision correction with pupil dependent correction having substantially decreased light scatter. The inner portion of the lens corresponding to inner dimension 20A may comprise a majority of the first plurality of echellettes 23A having the substantially monofocal near vision correction. For example, the substantially monofocal near vision echellettes may comprise a substantial majority composed of about 75% of the echellettes of the inner portion, and the substantially monofocal far vision echellettes may comprise a minority composed of about 25% of the echellettes of the inner portion, such that the multifocal inner portion is composed of monofocal echellettes. The outer portion of the lens corresponding to outer annular dimension 20B may comprise a minority of the first plurality of echellettes 23A having the substantially monofocal near vision correction. For example, the substantially monofocal near vision echellettes may comprise a minority composed of about 25% of the echellettes of the outer portion, and the substantially monofocal far vision echellettes may comprise a substantial majority composed of about 75% of the echellettes of the outer portion, such that the multifocal outer portion is composed of monofocal echellettes.

Figure 4C:
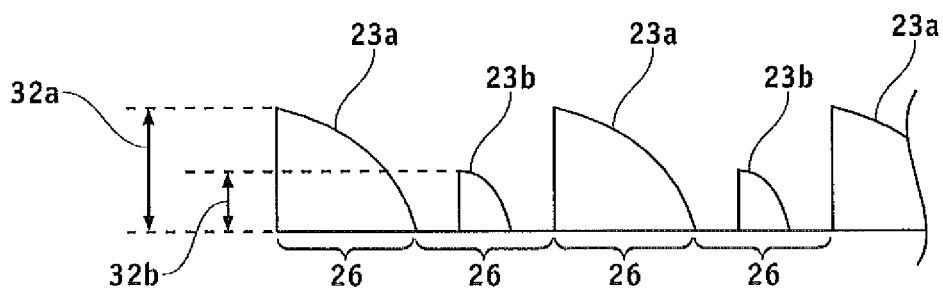
FIG. 4C shows a portion of a diffractive profile comprising the first plurality of echellettes having substantially monofocal diffractive profiles for near vision correction and the second plurality of echellettes having substantially bifocal diffractive profiles for far vision and intermediate vision correction, in accordance with embodiments.

FIG. 4C shows a portion of a diffractive profile of diffractive structure 10 comprising the first plurality of echellettes 23A having substantially monofocal diffractive profiles for near vision correction and the second plurality of echellettes 23B having substantially bifocal diffractive profiles for far vision and intermediate vision correction. The first step height 32A has K1=2 and corresponds to 2λ, with a physical step height of about 2λ/(Δη), as described above. The second step height 32B has K1=1 and corresponds to 1λ with a physical step height of about 2λ(Δη). Although the step height of the second plurality of echellettes corresponds to λ and diffracts a substantial amount of light energy to the first order corresponding to intermediate vision correction, the diffractive profile of each echellette comprises a substantially zero height profile along at least about half of the full period zone 26, such that a substantial amount of light energy is diffracted to the $0^{th}$ order. Based on the teachings described herein a person of ordinary skill in the art can determine the amount of light energy diffracted to the first and zero orders and determine empirically the step height and size of the portion comprising a height of zero so as to diffract appropriate amounts of light to the first order for intermediate vision correction and far vision correction.

When the first substantially monofocal diffractive profile providing near vision correction corresponds to 2λ and comprises first step height 32A of 2λ/(Δη), the second diffractive profile can diffract light to the first order and the zero order so as to provide the intermediate and far vision correction, respectively. The proportion of the first plurality of echellettes to the second plurality of echellettes can change radially so as to vary radially the amount of light energy to the near vision correction and the amount of light energy to the intermediate and far vision correction. The step height 32B of the second plurality of echellettes can also vary, for example with apodization, so as to vary the amount of light energy diffracted to the first order and zero order corresponding to the intermediate and far vision. For example to configure the multifocal second diffractive profile so as to provide a majority of far vision correction and a minority of intermediate vision correction, the second step height 32B can correspond to less than λ/2 and comprise a physical step height of less than λ/(Δη).

Figure 4D:
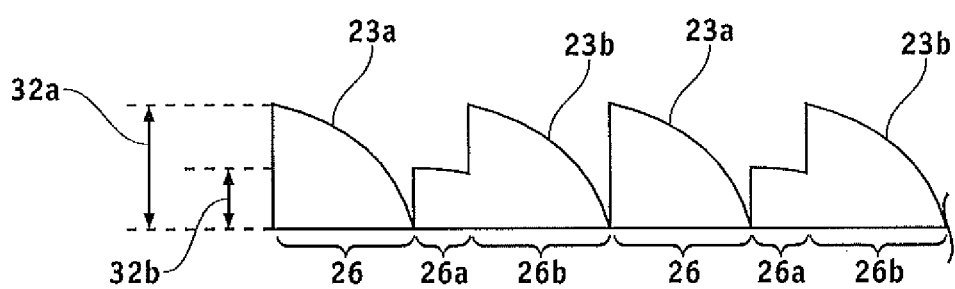
FIG. 4D shows a portion of a diffractive profile comprising the first plurality of echellettes having substantially monofocal diffractive profiles for near vision correction and a second plurality of echellettes providing intermediate and far vision correction, in accordance with embodiments.

FIG. 4D shows a portion of a diffractive profile of diffractive structure 10 comprising the first plurality of echellettes 23A having substantially monofocal diffractive profiles for near vision correction and a second plurality of echellettes 23B providing intermediate and far vision correction. The first step height 32A has K1=1 and corresponds to 1λ with a physical step height of about 1λ/(Δη), as described above. The second step height 32B has K2=½ and corresponds to ½λ, with a physical step height of about λ(Δη). As noted above, each of the plurality of full period zones 26 may comprise a first half period zone 26A and a second half period zone 26B, A first portion of each of the second echellettes 23B is located on first half period zone 26A, and a second portion of each of the second echellettes is located on the second half period zone 26B. The first portion comprises a first height corresponding to step height 32B and the second portion comprises a second height corresponding to step height 32A. The second plurality of echellettes 23B can diffract light to an intermediate focus and a distance focus with the step height 32B and the step height 32A.

Figure 4E:
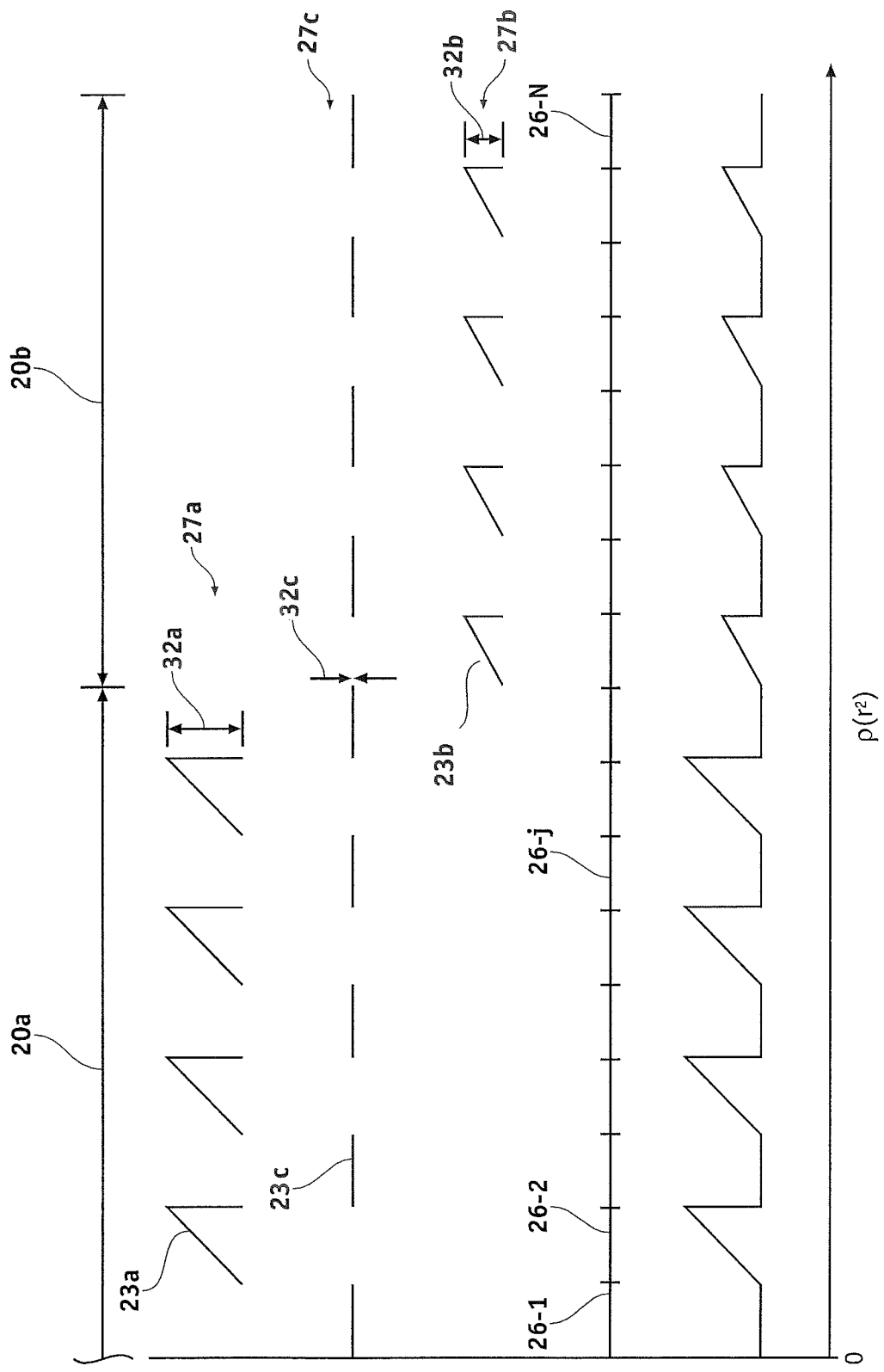
FIG. 4E shows a multifocal diffractive profile comprising a first plurality of substantially monofocal echellettes comprising a step height corresponding to about $2\lambda$ for near vision correction, a second plurality of substantially monofocal echellettes comprising a step height corresponding to about $1\lambda$ for intermediate vision correction, and a third plurality of echellettes comprising a step height corresponding to about $0\lambda$ for far vision correction, in accordance with embodiments.

FIG. 4E shows a multifocal diffractive profile 27 of diffractive structure 10 comprising a first plurality of substantially monofocal echellettes, a second plurality of substantially monofocal echellettes, and a third plurality of substantially monofocal echellettes. The first plurality of echellettes 23A comprises a substantially monofocal diffractive profile 27A having first step height 32A corresponding to about 2λ, for near vision correction. The second plurality of echellettes 23B comprises a substantially monofocal diffractive profile 27B having step second height 32B corresponding to about 1λ for intermediate vision correction. A third plurality of echellettes 23C comprises substantially monofocal diffractive profile 27C having a third step height 32C corresponding to about 0λ for far vision correction.

Figure 4F:
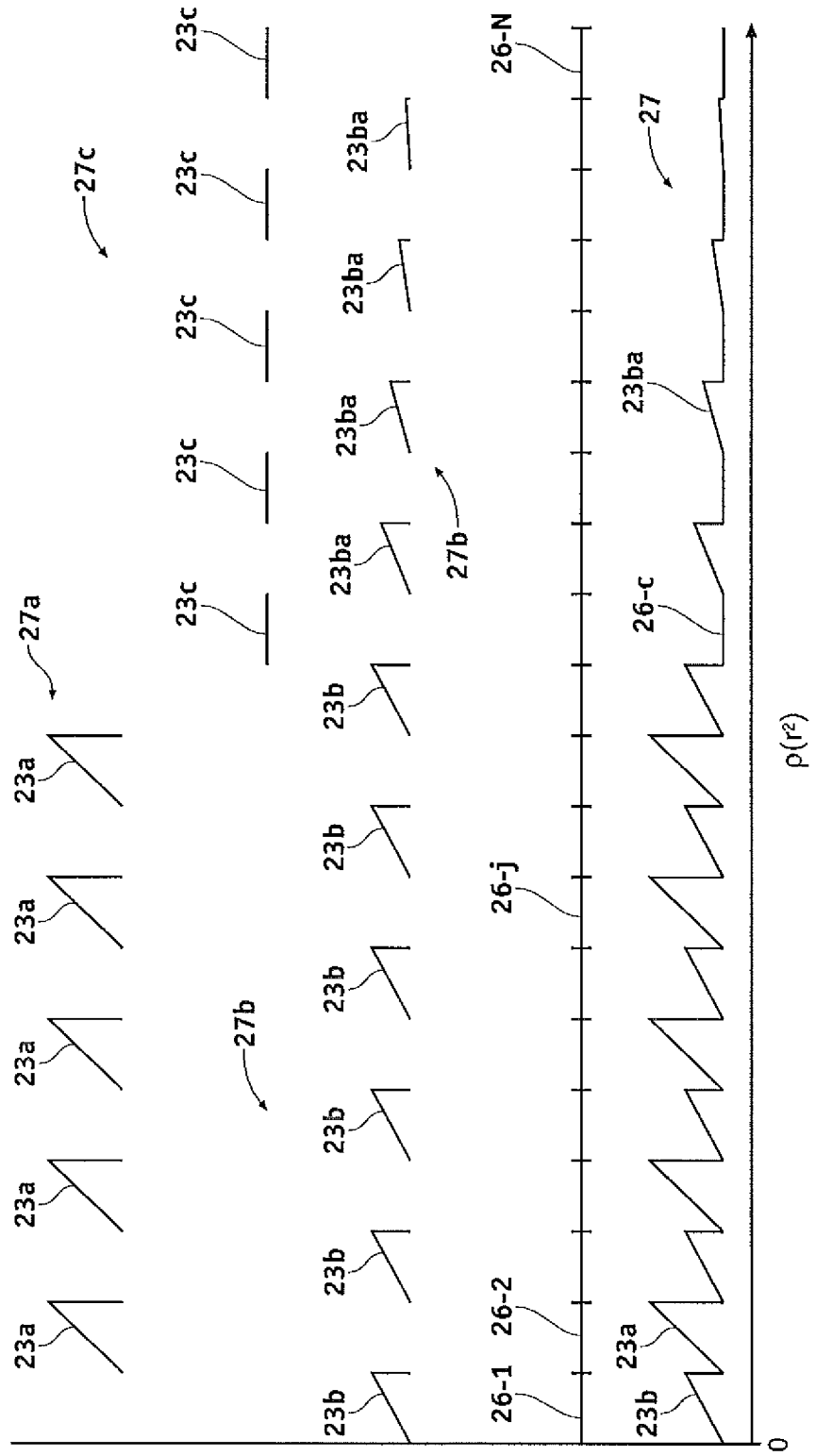
FIG. 4F shows a multifocal diffractive profile comprising a first plurality of substantially monofocal diffractive echellettes, and a second plurality of bifocal echellettes in which the second plurality of echellettes are apodized toward the periphery of the lens to provide far vision correction near the edge of the lens, in accordance with embodiments.

FIG. 4F shows a multifocal diffractive profile 27 of diffractive structure 10 comprising a first plurality of substantially monofocal diffractive echellettes 23A, a second plurality of bifocal echellettes 23B, and a third plurality of substantially monofocal echellettes 23C. The second plurality of bifocal echellettes 23B can be apodized toward the periphery of the lens to provide far vision correction near the edge of the lens. The first plurality of echellettes 23A comprises a substantially monofocal diffractive profile 27A having step second height 32A corresponding to about 1λ for near vision correction. The second plurality of echellettes 23B comprises a bifocal diffractive profile 27B having step second height 32B corresponding to a range from greater than about 0λ to less than about 1λ, for near and far vision correction, for example within a range from about ½λ, to about ¾λ. The multifocal diffractive profile comprises a third plurality of substantially monofocal echellettes 23C having a step height of approximately zero for substantially monofocal far vision correction. The third plurality of substantially monofocal echellettes comprises a third diffractive profile 27C.

The first substantially monofocal diffractive profile 27A comprising monofocal echellettes 23A can be combined with the bifocal second diffractive profile 27B comprising bifocal echellettes 23B and combined with the substantially monofocal third diffractive profile 27C comprising monofocal echellettes 23C so as to provide pupil dependent near and far vision correction with multifocal diffractive profile 27. The inner portion corresponding to dimension 20A may comprise the first substantially monofocal echellettes for near vision correction 23A, and the second plurality of bifocal echellettes 23B providing about half near vision correction and about half far vision correction, such that the inner portion comprises about 75% near vision correction and about 25% far vision correction. The outer portion corresponding to annular dimension 20B may comprise about half far vision correction echellettes 23C and about half bifocal echellettes 23B, in which the bifocal echellettes are apodized so as to decrease the near vision correction and increase the far vision correction. The correction of the outer portion near the inner portion may comprise about 25% near vision correction and 75% far vision correction varies radially outward away from the inner portion so as to change to about 90% far vision correction and about 10% near vision correction near the periphery.

Table I shows a diffractive profile comprising a first plurality of substantially monofocal echellettes and a second plurality of substantially monofocal echellettes that can provide pupil dependent correction with decrease light scatter and chromatic aberration, for example.

TABLE I

Multifocal Diffractive Echellette Profile

| Full period zone (j) | Echellette Type | Echellette Height (λ) |
|---|---|---|
| 1 | Monofocal/near | 1 |
| 2 | Monofocal/near | 1 |
| 3 | Monofocal/near | 1 |
| 4 | Monofocal/near | 1 |
| 5 | Monofocal/far | 0 |

TABLE I-continued

Multifocal Diffractive Echellette Profile

| Full period zone (j) | Echellette Type | Echellette Height (λ) |
|---|---|---|
| 6 | Monofocal/near | 1 |
| 7 | Monofocal/near | 1 |
| 8 | Monofocal/near | 0 |
| 9 | Monofocal/near | 1 |
| 10 | Monofocal/far | 0 |
| 11 | Monofocal/near | 1 |
| 12 | Monofocal/near | 0 |
| 13 | Monofocal/near | 1 |
| 14 | Monofocal/near | 0 |
| 15 | Far/far | 0 |
| 16 | Far/far | 1 |
| 17 | Far/far | 0 |
| 18 | Far/far | 0 |
| 19 | Far/far | 0 |
| 20 | Far/far | 1 |
| 21 | Far/far | 0 |
| 22 | Far/far | 0 |
| 23 | Far/far | 0 |
| 24 | Far/far | 0 |

Table II shows echellettes having optical powers of 4D, 2D, 1D and corresponding full period zones suitable for combination based on the full period zones of the add power Da for near vision correction. The profiles of the substantially monofocal echellettes of Table II may comprise step heights and transition zones as described herein. The full period zones of Da for the near vision correction can be combined in many ways with the echellettes for far and intermediate vision so as to provide a multifocal lens comprising of a first plurality of substantially monofocal echellettes for near vision correction, a second plurality of substantially monofocal echellettes for far vision correction, a third plurality of echellettes for intermediate vision correction, and a fourth plurality of echellettes for another intermediate vision correction. For a given near vision correction, such as 4D of add power (hereinafter "Da"), the amount of add optical power of the intermediate vision correction corresponds an inverse integer multiple (hereinafter "M") of the add correction, e.g. Da/2 or Da/3, or combinations thereof.

TABLE II

| 4D | | | 2D | | | 1D | | |
|---|---|---|---|---|---|---|---|---|
| Full period zone (j) | r | $\hat{r}2$ | Full period zone (j) | r | $\hat{r}2$ | Full period zone (j) | r | $\hat{r}2$ |
| 0 | 0 | 0 | | | | | | |
| 1 | 0.524 | 0.275 | | | | | | |
| 2 | 0.741 | 0.549 | 1 | 0.741 | 0.549 | | | |
| 3 | 0.908 | 0.824 | | | | | | |
| 4 | 1.048 | 1.098 | 2 | 1.048 | 1.098 | 1 | 1.048 | 1.098 |
| 5 | 1.172 | 1.373 | | | | | | |
| 6 | 1.284 | 1.647 | 3 | 1.284 | 1.647 | | | |
| 7 | 1.386 | 1.922 | | | | | | |
| 8 | 1.482 | 2.197 | 4 | 1.482 | 2.197 | 2 | 1.482 | 2.197 |
| 9 | 1.572 | 2.471 | | | | | | |
| 10 | 1.657 | 2.746 | 5 | 1.657 | 2.746 | | | |
| 11 | 1.738 | 3.020 | | | | | | |
| 12 | 1.815 | 3.295 | 6 | 1.815 | 3.295 | 3 | 1.815 | 3.295 |
| 13 | 1.889 | 3.569 | | | | | | |
| 14 | 1.961 | 3.844 | 7 | 1.961 | 3.844 | | | |
| 15 | 2.029 | 4.119 | | | | | | |
| 16 | 2.096 | 4.393 | 8 | 2.096 | 4.393 | 4 | 2.096 | 4.393 |
| 17 | 2.161 | 4.668 | | | | | | |
| 18 | 2.223 | 4.942 | 9 | 2.223 | 4.942 | | | |
| 19 | 2.284 | 5.217 | | | | | | |
| 20 | 2.343 | 5.492 | 10 | 2.343 | 5.492 | 5 | 2.343 | 5.492 |

TABLE II-continued

| 4D | | | 2D | | | 1D | | |
|---|---|---|---|---|---|---|---|---|
| Full period zone (j) | r | $\hat{r}2$ | Full period zone (j) | r | $\hat{r}2$ | Full period zone (j) | r | $\hat{r}2$ |
| 21 | 2.401 | 5.766 | | | | | | |
| 22 | 2.458 | 6.041 | 11 | 2.458 | 6.041 | | | |
| 23 | 2.513 | 6.315 | | | | | | |
| 24 | 2.567 | 6.590 | 12 | 2.567 | 6.590 | 6 | 2.567 | 6.590 |
| 25 | 2.620 | 6.864 | | | | | | |
| 26 | 2.672 | 7.139 | 13 | 2.672 | 7.139 | | | |
| 27 | 2.723 | 7.414 | | | | | | |
| 28 | 2.773 | 7.688 | 14 | 2.773 | 7.688 | 7 | 2.773 | 7.688 |
| 29 | 2.822 | 7.963 | | | | | | |
| 30 | 2.870 | 8.237 | 15 | 2.870 | 8.237 | | | |
| 31 | 2.918 | 8.512 | | | | | | |
| 32 | 2.964 | 8.786 | 16 | 2.964 | 8.786 | 8 | 2.964 | 8.786 |

The optical power Di of the intermediate echellettes can be inversely related to the width of intermediate echellette when the height of the intermediate echellette substantially approximates the height of the first plurality of substantially monofocal echellettes for near vision correction, for example when the heights of the substantially monofocal echellettes correspond to about 1λ. In many embodiments $$Di = Da/M$$

where Di is the intermediate optical power and M is the width integer multiple of the substantially monofocal intermediate vision echellette determined based on the widths of the corresponding full period zones of the substantially monofocal near vision correction echellettes. As can be seen with reference to Table II, when Da is 4D and M is 2, Di is about 2D and the width of the intermediate vision echellette corresponds to about two full period zones. When M is 4 and Da is about 4D, Di is about 1 D and the width of the intermediate vision echellette correspond to about 4 full period zones. When Da is about 4D and M is 3, Di is about 1.33 D and the width of the intermediate vision echellette corresponds to about three full period zones.

The far vision correction echellettes have a step height of about 0λ, for example +/−0.25λ, and are located one or more of the full period zones. Each of the intermediate vision correction echellettes is located so as to correspond to adjacent full period zones of echellettes of Da and has a width corresponding to the integer multiple M. For example, each of the Da/2 echellettes has an optical power of Da/2 and a width of corresponding 2 of the adjacent full period zones of Da.

Tables similar to Table II can be generated for many amounts of near, far and intermediate vision correction. For example, Da can be about 3D of add optical power, such that Da/2 is 1.5 D and Da/4 is about 0.75 D, and the widths corresponding to the optical power are two adjacent full period zones (M=2) and three adjacent full period zones (M=3), respectively. Although even integers are shown, similar results can be obtained with odd integers such as Da/3 corresponding to three full period zones and an optical power of Da/3, for example 1D when the add power for near vision correction is 3D.

Table III shows a multifocal diffractive profile comprising a first plurality of substantially monofocal echellettes having a first optical power for near vision correction, a second plurality of substantially monofocal echellettes having a second optical power for far vision correction, a third plurality of substantially monofocal echellettes having a third optical power for intermediate vision correction, and a fourth plurality of substantially monofocal echellettes having a fourth optical power for intermediate vision correction less than the third optical power, so as to provide pupil dependent near, far and intermediate vision correction with decreased light scatter and chromatic aberration.

TABLE III

Multifocal Diffractive Echellette Profile

| Full period Zone (j) | Corresponding Full period zone(s) of Near Vision Add Power (Da) | Corresponding Width of Full period zone(s) of Near Vision Add Power (Da) | Echellette Type | Echellette Height (λ) | Outer Radius | Add Power (D) |
|---|---|---|---|---|---|---|
| 1 | 1 | 1 | Monofocal/near | 1 | 0.524 | 4 |
| 2 | 2 | 1 | Monofocal/near | 1 | 0.741 | 4 |
| 3 | 3 | 1 | Monofocal/near | 1 | 0.908 | 4 |
| 4 | 4 | 1 | Monofocal/far | 0 | 1.048 | 0 |
| 5 | 5, 6 | 2 | Monofocal/int | 1 | 1.284 | 2 |
| 6 | 7 | 1 | Monofocal/far | 0 | 1.386 | 0 |
| 7 | 8 | 1 | Monofocal/near | 1 | 1.482 | 4 |
| 8 | 9, 10 | 2 | Monofocal/int | 1 | 1.657 | 2 |
| 9 | 11 | 1 | Monofocal/far | 0 | 1.738 | 0 |
| 10 | 12 | 1 | Monofocal/far | 0 | 1.815 | 0 |
| 11 | 13 | 1 | Monofocal/near | 1 | 1.889 | 4 |
| 12 | 14 | 1 | Monofocal/int | 1 | 1.961 | 2 |
| 13 | 15 | 1 | Monofocal/far | 0 | 2.029 | 0 |
| 14 | 16 | 1 | Monofocal/near | 1 | 2.096 | 4 |
| 15 | 17, 18 | 2 | Monofocal/int | 1 | 2.223 | 2 |
| 16 | 19 | 1 | Monofocal/near | 1 | 2.284 | 4 |
| 17 | 20 | 1 | Monofocal/far | 0 | 2.343 | 0 |
| 18 | 21 | 1 | Monofocal/near | 1 | 2.401 | 4 |
| 19 | 22 | 1 | Monofocal/far | 0 | 2.458 | 0 |
| 20 | 23 | 1 | Monofocal/near | 1 | 2.513 | 4 |
| 21 | 24 | 1 | Monofocal/far | 0 | 2.567 | 0 |
| 22 | 25 | 1 | Monofocal/near | 1 | 2.620 | 4 |
| 23 | 26 | 1 | Monofocal/far | 0 | 2.672 | 0 |
| 24 | 27 | 1 | Monofocal/near | 1 | 2.723 | 4 |
| 25 | 28 | 1 | Monofocal/far | 0 | 2.773 | 0 |
| 26 | 29, 30, 31, 32 | 4 | Monofocal/int | 1 | 2.964 | 1 |

The height of the first plurality of substantially monofocal echellettes and the third plurality of substantially monofocal echellettes is about 1λ, and the width of the third plurality of substantially monofocal echellettes corresponds to about twice the width of the first plurality. The height of the first plurality of substantially monofocal echellettes and the fourth plurality of substantially monofocal echellettes is about 1λ, and the width of the fourth plurality of substantially monofocal echellettes corresponds to about four times the width of the first plurality.

Figure 5:
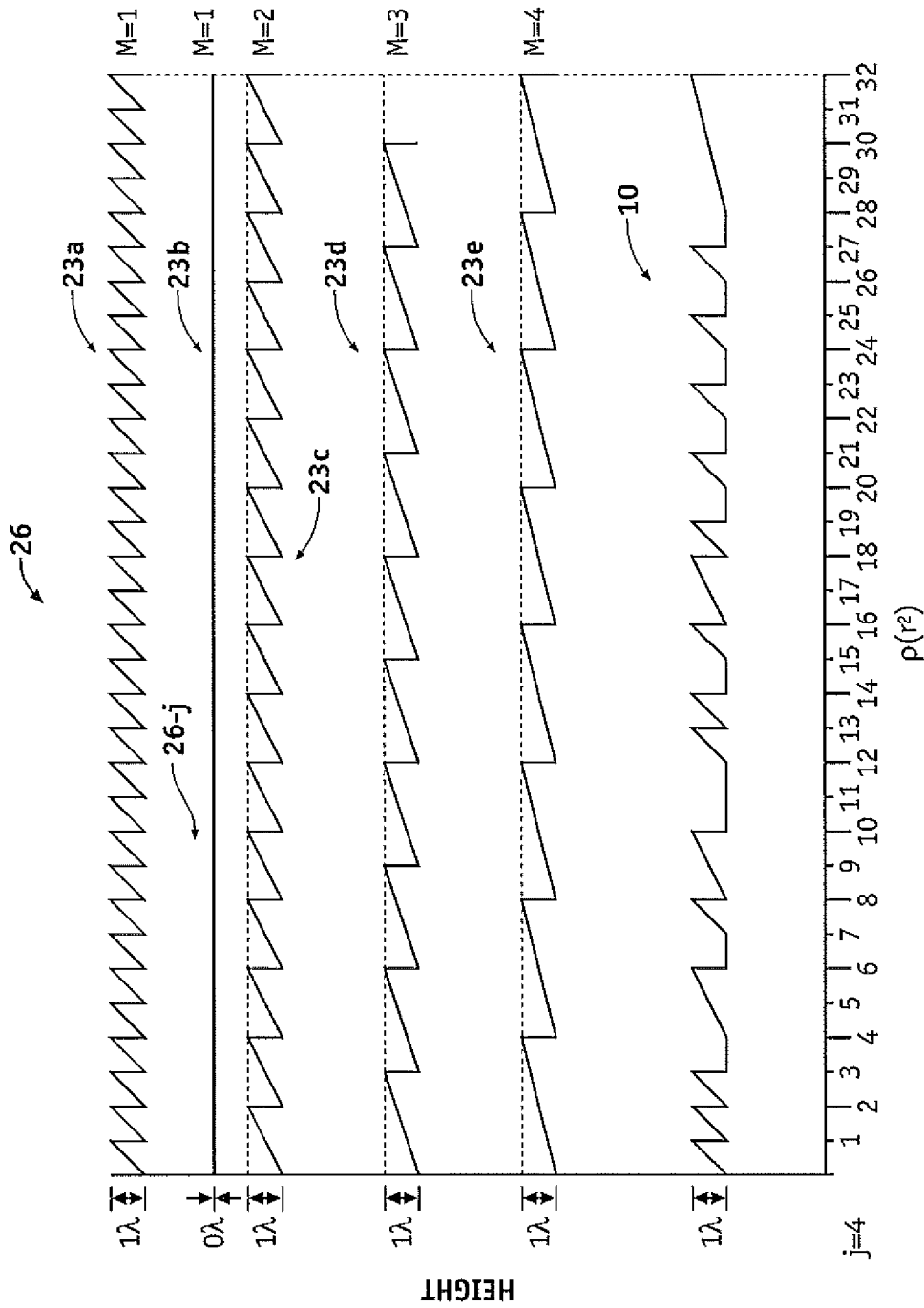
FIG. 5 shows substantially monofocal echellettes suitable for combination so as to provide a diffractive structure in accordance with embodiments.

FIG. 5 shows a substantially monofocal echellettes 23 suitable for combination so as to provide diffractive structure 10 in accordance with Table III. The first plurality of substantially monofocal echellettes 23A has a first optical power Da for near vision correction, a height of 1λ, and a width integer multiple M=1 so as to define a first plurality of full period zones 26. A second plurality of substantially monofocal echellettes 23B has a second optical power (Da=0) for far vision correction, a height of 1λ, and width integer multiple M=1. A third plurality of substantially monofocal echellettes 23C can be located on the plurality of full wave zones 26 and may have a third optical power (Da/2) for intermediate vision correction, a height of 1λ, a width integer multiple M=2, and widths corresponding to the width integer multiple of 2. A fourth plurality of substantially monofocal echellettes 23D can be located on the plurality of full wave zones 26 and may have a fourth optical power (Da/3) for intermediate vision correction, a height of 1λ, a width integer multiple M=3, and widths corresponding to the width integer multiple of 3. A fifth plurality of substantially monofocal echellettes 23E can be located on the plurality of full wave zones 26 and may have a fifth optical power (Da/4) for intermediate vision correction, a height of 1λ, a width integer multiple M=4, and widths corresponding to the width integer multiple of 4.

The diffractive structure 10 may comprise many combinations of the first through fifth plurality of echellettes located on the plurality of full period zones 26 so as to provide diffraction of at least about 90% to the viewing orders, for example 95% of the transmitted light energy to the viewing orders. The substantially monofocal echellettes may comprise smooth profiles having transition zones as described herein. The heights of the substantially monofocal echellettes corresponding to the integer multiple K of the design wavelength can be within about +/−0.25λ, for example within about +/−0.1λ, so as to achieve the transmission of at least about 90%, for example at least about 95%. These efficiencies of the substantially monofocal echellettes can be achieved with polychromatic visible light energy having wavelengths from about 400 nm to about 800 nm having a light energy distribution corresponding to solar irradiance.

The diffraction efficiencies as described herein were calculated using MATHCAD, available from Parametric Technology Corporation of Needham, Mass. The wavelength analyzed was about 500 nm, which is sufficiently far from the design wavelength of about 550 nm so as to correspond substantially to the diffraction of polychromatic substantially white light.

For illustration purposes, the profile geometries shown in the aforementioned figures may not be drawn exactly to scale. The heights of the diffractive profiles shown in the figures can generally in the order of about 0.5 millimeters and about 2.0 millimeters although the heights may vary depending on factors such as the amount of correction helpful to the patient, the refractive index of the lens material and surrounding medium, and the desired distribution of light between useful diffraction orders.

The embodiments described above, including accompanying drawings, figures, functions and tables, are for illustrative purposes to explain aspects of the present invention. Those skilled in the art will recognize that changes and modifications can be made without departing from the scope of the invention. Therefore, the scope of the present invention shall be limited solely by the full scope of the following claims.

What is claimed is:

1. A method of correcting vision of an eye, the method comprising:
   placing a lens along an optical path of the eye, the lens comprising at least one curved surface coupled to a diffractive structure, the diffractive structure comprising a first plurality of substantially monofocal echellettes having a first optical power for a near vision correction and a second plurality of substantially monofocal echellettes having a second optical power for a far vision correction;
   wherein the first plurality of substantially monofocal echellettes diffracts transmitted light with a first efficiency of at least about 90% for the near vision correction and the second plurality of substantially monofocal echellettes diffracts transmitted light with an efficiency of at least about 90% for the far vision correction,
   wherein the first plurality of substantially monofocal echellettes has a corresponding first plurality of full period zones and wherein the second plurality of substantially monofocal echellettes has a second plurality of full period zones corresponding to the first plurality of full period zones,
   wherein the diffractive structure comprises a third plurality of substantially monofocal echellettes having an intermediate optical power for an intermediate vision correction, the third plurality of substantially monofocal echellettes having third heights approximating first heights of the first plurality of substantially mono focal echellettes, the third plurality of substantially monofocal echellettes having a third plurality of full period zones corresponding to the first plurality of full period zones, the first plurality of full period zones having first widths and the third plurality of full period zones having third widths, the third widths corresponding to an integer multiple of two or more of the first widths such that first optical power corresponds to the integer multiple multiplied with the third optical power.

2. The method of claim 1, wherein the diffractive structure is imposed on the at least one curved surface.

3. The method of claim 1, wherein the first plurality of substantially monofocal of echellettes extends substantially around an inner boundary and an outer boundary of each of substantially monofocal echellettes of the second plurality.

4. The method of claim 3, wherein the first height of the first plurality of substantially monofocal echellettes corresponds to a non-zero integer multiple of a design wavelength and wherein the second plurality of echellettes comprises a second step height of about zero and wherein the first plurality of substantially monofocal echellettes extends substantially along the inner boundary and the outer boundary so as to define said each of the second plurality of substantially monofocal echellettes.

5. The method of claim 1, wherein the first plurality of substantially monofocal echellettes and an optical zone size of the diffractive structure determine an integer number of full period zones, the integer number of full period zones comprising the first plurality of full period zones and the second plurality of full period zones.

6. The method of claim 5, wherein the first plurality of substantially monofocal echellettes is determined based on the first optical power, the optical zone size, a design wavelength and a difference of an index of refraction of the eye and an index of refraction of the diffractive structure.

7. The method of claim 5, wherein the first plurality of substantially monofocal echellettes comprises first substantially monofocal diffractive profiles extending substantially across the first plurality of full period zones and the second plurality of substantially monofocal echellettes comprises second substantially monofocal diffractive profiles extending substantially across the second plurality of full period zones and wherein the second plurality of full period zones have sizes and locations based on the first plurality of full period zones.

8. The method of claim 1, wherein the diffractive structure comprises an inner portion and an outer portion, the inner portion comprising an inner portion of the first plurality of substantially monofocal echellettes to the second plurality of substantially monofocal echellettes, the outer portion comprising an outer proportion of the first plurality of substantially monofocal echellettes to the second plurality of substantially monofocal echellettes, the outer proportion less than the inner proportion so as to provide near vision correction with the inner portion and far vision correction with outer portion when the pupil responds to light.

9. The method of claim 1, wherein the diffractive structure has full period zones comprising pairs of half period zones, wherein each of the pairs comprises an inner half period zone having an inner phase and an outer half period zone having an outer phase opposite the inner phase, and
   wherein the third plurality of echellettes comprises pairs of echellettes, each pair having an inner echellette extending substantially across the inner half period zone and an outer echellette extending substantially across the outer half period zone.

* * * * *